(12) United States Patent
Heuser et al.

(10) Patent No.: US 8,206,920 B2
(45) Date of Patent: Jun. 26, 2012

(54) DIAGNOSTIC ASSAY FOR THE SPECIFIC TREATMENT OF ACUTE MYELOID LEUKEMIA

(75) Inventors: Michael Heuser, Vancouver (CA); Arnold Ganser, Hannover (DE); Konstanze Döhner, Neu-Ulm (DE); Richard Schlenk, Ulm (DE)

(73) Assignees: Arnold Ganser, Hannover (DE); Michael Heuser, Hannover (DE)

( * ) Notice: Subject to any disclaimer, the term of this patent is extended or adjusted under 35 U.S.C. 154(b) by 1337 days.

(21) Appl. No.: 11/728,505

(22) Filed: Mar. 26, 2007

(65) Prior Publication Data

US 2009/0197953 A1    Aug. 6, 2009

(51) Int. Cl.
*C12Q 1/68* (2006.01)
(52) U.S. Cl. .................... 435/6.11; 435/6.12; 435/6.14
(58) Field of Classification Search .................... None
See application file for complete search history.

(56) References Cited

U.S. PATENT DOCUMENTS 5,582,822 A * 12/1996 Brandely et al. ............. 424/85.2
2005/0202451 A1* 9/2005 Burczynski et al. ............. 435/6

FOREIGN PATENT DOCUMENTS

EP          1454994 A1 *  9/2004

OTHER PUBLICATIONS

Profile Quant™ Leukaemia, ProfileQuant™ WT1 Kit (2004).
E. Beillard et al., "Evaluation of candidate control genes for diagnosis and residual disease detection in leukemic patients using 'real-time' quantitative reverse-transscriptase polymerase chain reaction (RQ-PCR)—a Europe against cancer program", Leukemia (2003) 17, pp. 2474-2486.
J. Gabert et al., "Standardization and quality control studies of 'real-time' quantitative reverse transcriptase polymerase chain reaction of fusion gene transcripts for residual disease detection in leukemia—a Europe Against Cancer Program", Leukemia (2003) 17, pp. 2318-2357.
M. Heuser et al., "High meningioma 1 (MNI) expression as a predictor for poor outcome in acute myeloid leukemia with normal cytogenetics", Blood, Dec. 1, 2006—vol. 108, No. 12, pp. 3898-3905.
A. Belhabri et al., "All *trans* retinoic acid in combination with intermediate-dose cytarabine and idarubicin in patients with relapsed or refractory non promyelocytic acute myeloid leukemia: a phase II randomized trial", The Hematology Journal (2002) 3, pp. 49-55.
E. Estey et al., "Randomized Phase II Study of Fludarabine + Cytosine Arabinoside + Idarubicin ± All-Trans Retinoic Acid ± Granulocyte Colony-Stimulating Factor in Poor Prognosis Newly Diagnosed Acute Myeloid Leukemia and Myelodysplastic Syndrom", Blood, vol. 93, No. 8 Apr. 15, 1999; pp. 2478-2484.
D. Milligan et al., "Fludarabine and cytosine are less effective than standard ADE chemotherapy in high-risk acute myeloid leukemia, and addition of G-CSF and ATRA are not beneficial: results of the MRC AML-HR randomized trial", Blood Jun. 15, 2006, vol. 107, No. 12, pp. 4614-4622.
K. van Wely, et al., "The MN1 oncoprotein synergizes with coactivators RAC3 and p300 in RAR-RXR-mediated transcription", Oncogene (2003) 22, pp. 699-709.

* cited by examiner

*Primary Examiner* — Gyan Chandra
(74) *Attorney, Agent, or Firm* — Greer, Burns & Crain Ltd.

(57) ABSTRACT

The present invention provides the use of all-trans retinoic acid for the production of a pharmaceutical composition for the treatment of acute myeloid leukemia, which use is characterized in that the patients are selected from the group of non-M3 acute myeloid leukemia patients according to a physiologic concentration, e.g. a level of MN1 below a certain critical level analysed in total blood cells, preferably analysed in bone marrow cells. The critical level of MN1 can be determined according to known methods, e.g. by specific determination of the presence of MN1, e.g. using specific anti-MN1 antibody, e.g. in an ELISA or in another immuno specific assay. Preferably, the level of MN1 is determined at its transcription level, e.g. as the concentration of mRNA encoding MN1.

10 Claims, 3 Drawing Sheets

DIAGNOSTIC ASSAY FOR THE SPECIFIC TREATMENT OF ACUTE MYELOID LEUKEMIA

Figure 1:
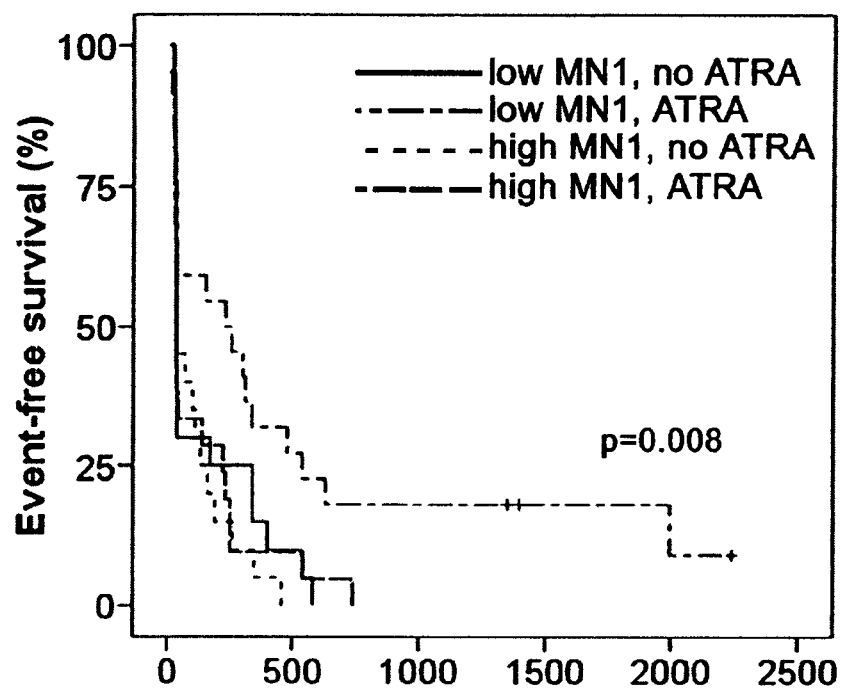

The present invention relates to the use of all-trans retinoic acid for the production of a pharmaceutical composition for the specific treatment of acute myeloid leukemia excluding the M3 subtype. All-trans retinoic acid is, according to the invention, used in the therapy of acute myeloid leukemia and, accordingly, the present invention also relates to the specific treatment of patients suffering from acute myeloid leukemia excluding the M3 subtype.

The specificity of the treatment of acute myeloid leukemia using all-trans retinoic acid refers to the selection of patients in which the treatment with all-trans retinoic acid has a high probability of efficacy.

In a further aspect, the present invention relates to be a diagnostic assay and to the use of compounds for the production of a diagnostic assay aiming at the identification of the group of acute myeloid leukemia patients for the selection of a sub-group of these patients.

In accordance with the specificity of the use of all-trans retinoic acid for use in the production of a pharmaceutical composition for the treatment of acute myeloid leukemia patients having a certain level of a specific marker, the diagnostic assay according to the present invention is used for the determination of the relevant group of acute myeloid leukemia patients according to the invention, i.e. to the determination of the level of the specific marker.

STATE OF THE ART

Heuser et al. (Blood, Vol. 108, No. 12, 3898-3905) describe that a high level of expression of meningioma 1 (MN1) is an indicator for predicting a poor outcome of conventional induction chemotherapy in acute myeloid leukemia patients having normal cytogenetics. Apart from the known role of MN1 being a target of vitamin $D_3$ in osteoblasts, inhibiting their proliferation, and in addition to the mouse knock-out model of MN1 demonstrating that MN1 plays a crucial role in cranial bone development, it is assumed that MN1 plays a role both in normal hematopoiesis and in leukemia. Induction therapy consisted of administration of idarubicin, etoposide and cytosine-arabinoside for all patients, followed by a second course of idarubicin, etoposide and cytosine-arabinoside. In the alternative to the second course of this induction therapy, a therapeutic regimen termed FLAG-Ida (comprising fludarabin in combination with cytosine-arabinoside, granulocyte colony-stimulating factor (G-CSF), and idarubicin) was used for patients with a poor response to the first course of induction therapy. For consolidation therapy, cytosine-arabinoside and daunorubicin were administered, or a second course of FLAG-Ida, respectively, for patients responding to the first stage of induction therapy or patients responding to the previous therapy of FLAG-Ida.

Van Wely et al. (Oncogene, 22:699-709 (2003)) describe that MN1 binds to retinoic acid response elements and that MN1 synergizes with all-trans retinoic acid to activate the transcriptional activity of the Moloney sarcoma virus long terminal repeat.

To-date, acute myeloid leukemia patients being diagnosed with the M3 subtype are presently treated with all-trans retinoic acid with a good success rate. Currently, non-M3 acute myeloid leukemia is generally considered not to be curable by a treatment with all-trans retinoic acid.

At present, no predictive marker is known that can be correlated with a therapeutic effect of all-trans retinoic acid in the treatment of acute myeloid leukemia not being classified as M3 subtype. As a consequence, it is observed that the treatment of non-M3 acute myeloid leukemia patients with all-trans retinoic acid in a significant fraction of the patients, only leads to the serious side effects of the all-trans retinoic acid treatment, without significantly improving the health status of these patients. Further, the current opinion, e.g. represented by Milligan et al. (Blood 107, 4614-4622 (200)), Belhabri et al. (Hematol. J. 3, 49-55 (2002)), and Estey et al. (Blood 93, 2478-2484 (1999)) can result in denying treatment with all-trans retinoic acid to the small fraction of non-M3 acute myeloid leukemia patients that has been found by the present inventors to have at least some prospects for a positive effect of treatment by all-trans retinoic acid.

OBJECTS OF THE INVENTION

In view of the essentially ineffective treatment of a fraction of non-M3 acute myeloid leukemia patients using all-trans retinoic acid as a pharmaceutically active compound, the present invention aims at providing an improved treatment of non-M3 acute myeloid leukemia patients with all-trans retinoic acid, e.g. based on the use of all-trans retinoic acid as a component of a pharmaceutical composition, characterized by the selection of non-M3 acute myeloid leukemia patients that positively respond to the all-trans retinoic acid treatment.

Further, the present invention aims at providing a diagnostic assay and to the use of compounds for production of the diagnostic assay, suitable for the determination of the sub-group of non-M3 acute myeloid leukemia patients that respond to a treatment using all-trans retinoic acid from the group of all acute myeloid leukemia patients.

SUMMARY

In one embodiment, the invention relates to the use of all-trans retinoic acid for the production of a pharmaceutical composition for the treatment of acute myeloid leukemia excluding the M3 subtype, wherein that the patient being diagnosed with acute myeloid leukemia has a physiological level of MN1 below a critical level defined by a value of 0.06 to 0.07, preferably of 0.066 determined for the quotient of the concentration of MN1 transcripts to the concentration of ABL transcripts for the same patient sample. In respect of transcripts, the terms concentration and copy number are used interchangeably. It is preferred that the concentration of MN1 is analysed using the polymerase chain reaction with at least one pair of primers specific for the amplification of at least a fraction of a nucleic acid sequence encoding MN1 on the basis of cDNA produced on the basis of total RNA of a patient sample. Preferably, the treatment comprises the treatment according to the AML HD98-B protocol.

Further, the invention relates to the use of compounds for the production of a diagnostic assay kit for the determination of the concentration of MN1 expression, wherein the sample to be assayed is obtained from a patient being diagnosed with acute myeloid leukemia excluding the M3 subtype. The maximum level of MN1, considered according to the invention to be indicative of improved healing prospects of a patient subjected to a therapy implying the administration of all-trans retinoic acid, is set at 0.06 to 0.07, preferably 0.066, for the concentration of MN1 transcripts to transcripts from the ABL gene. Preferably, the treatment of acute myeloid leukemia excluding the M3 subtype comprising the administration of all-trans retinoic acid, wherein the patient being diagnosed with acute myeloid leukemia has a physiological level of MN1 below a critical level defined by a value of 0.06 to 0.07, preferably 0.066 determined for the quotient of the concentration of MN1 transcripts to the concentration of ABL transcripts for the same patient sample. This treatment can be combined with a concentration of MN1 being analysed using the polymerase chain reaction with at least one pair of primers specific for the amplification of at least a fraction of a nucleic acid sequence encoding MN1 on the basis of cDNA produced on the basis of total RNA of a body sample. Further, the treatment according can comprise the administration of pharmaceutically active compounds according to the AML HD98-B protocol.

GENERAL DESCRIPTION OF THE INVENTION

The present invention achieves the above-mentioned objects by providing the use of all-trans retinoic acid for the production of a pharmaceutical composition for the treatment of acute myeloid leukemia, which use is characterized in that the patients are selected from the group of non-M3 acute myeloid leukemia patients according to a physiologic concentration, e.g. a level of MN1 below a certain critical level analysed in total blood cells, preferably analysed in bone marrow cells. The critical level of MN1 can be determined according to known methods, e.g. by specific determination of the presence of MN1, e.g. using specific anti-MN1 antibody, e.g. in an ELISA or in another immuno specific assay. Preferably, the level of MN1 is determined at its transcription level, e.g. as the concentration of mRNA encoding MN1. The MN1-specific assay can be performed on samples of body fluid or tissue, preferably on a blood sample, more preferably on a bone marrow sample.

The present invention is based on the observation that presence of a high level of MN1, e.g. determined as a high concentration of MN1 specific transcripts in blood, correlates with a significantly lower efficacy of the treatment of acute myeloid leukemia using all-trans retinoic acid. In contrast, a level of MN1 below a critical level according to the invention, e.g. determined as MN1 protein or as MN1-specific mRNA in blood, correlates with significantly higher efficacy of the treatment of acute myeloid leukemia using all-trans retinoic acid. Preferably, the critical level of MN1 is determined in relation to an internal reference protein or RNA of the patient sample, the reference protein and RNA, respectively, being used for normalization of the level of MN1, e.g. by forming the quotient of the level of MN1 and reference level.

Preferably, the group of acute myeloid leukemia patients is further restricted to non-M3 acute myeloid leukemia patients, i.e. excluding the M3 subtype.

In a first aspect, the present invention provides the use of all-trans retinoic acid (ATRA) for the production of a pharmaceutical composition for the treatment of acute myeloid leukemia, which acute myeloid leukemia correlates with a physiologic level of MN1 below a critical level. Accordingly, the use of all-trans retinoic acid for the production of a pharmaceutical composition according to the present invention is characterized by the selection of patients having a physiological level of MN1 below the critical level.

In accordance with the use of all-trans retinoic acid for the production of a pharmaceutical composition according to the present invention, there is also provided the treatment of acute myeloid leukemia in patients, which patients are characterized in having a physiologic level of MN1 below a critical level. In these patients, the positive effect of the treatment of acute myeloid leukemia with all-trans retinoic acid correlates with a physiologic level of MN1 below the critical level.

The critical physiologic level of MN1 is a discriminating indicator for the efficacy of the treatment using all-trans retinoic acid for the medical indication of acute myeloid leukemia with a physiologic level of MN1 below the critical level being indicative of a significantly higher treatment efficacy, e.g. good healing prospects, whereas a physiologic level of MN1 above the critical level is indicative of significantly reduced efficacy of the treatment of acute myeloid leukemia using all-trans retinoic acid.

Accordingly, the present invention provides the advantage for patients in which the acute myeloid leukemia does not respond to treatment with all-trans retinoic acid, that the unnecessary burden and side effects of the all-trans retinoic acid treatment can be avoided. For patients of a non-M3 subtype of acute myeloid leukemia, in which hitherto treatment with all-trans retinoic acid only in a small fraction of patients was successful, the present invention provides the advantage that they can be identified according their level of MN1 below the critical level as this indicator could be shown to be a sound basis for a positive prognosis of a successful treatment with all-trans retinoic acid. Accordingly, the fraction of acute myeloid leukemia patients that can be treated with all-trans retinoic acid with a good reasoning for success can now be identified even if they have been classified as not belonging to the M3 subtype.

Preferably, the physiologic concentration of MN1 for defining the group of patients according to the present invention is based on the use of an in vitro assay for the determination of the physiologic concentration of MN1 in acute myeloid leukemia patients and classifying the diagnosed MN1 concentration to a value below the critical level.

In a second aspect, the present invention relates to a diagnostic assay and to the use of compounds for the production of a diagnostic assay kit for the determination of the level of MN1 in acute myeloid leukemia patients. For selecting the group of acute myeloid leukemia patients according to the present invention, the level of MN1 is classified to a value below the critical level of MN1.

For the present invention, the critical level of MN1 is preferably determined as the median level of a statistically relevant group of acute myeloid leukemia patients, excluding patients diagnosed with the M3 subtype. The determination of MN1 concentration, i.e. the concentration of the MN1 gene product, is preferably made in relation to the concentration of a reference gene product naturally present in a patient sample.

Preferably, the level of MN1 is determined as the concentration of transcripts of mRNA encoding MN1, i.e. the concentration transcripts of the MN1 gene. This level or concentration, respectively, is preferably determined by polymerase chain reaction (PCR) including reverse transcription (RT) using primers specific on total RNA encoding MN1 obtained from the patient. The PCR can comprise nested amplification, e.g. a first PCR reaction using a first set of primers to produce a first amplification product having sequences specific for MN1, followed by a second PCR using a second set of primers specific for and hybridizing to the amplification product of the first PCR, which second set of primers partially, preferably completely exclude the sequences of the first set of primers. Preferably, the specificity of the PCR is increased by adding a fluorescent probe to the assay, which is e.g. known from quantitative PCR methods.

For the determination of transcript concentration, it is preferred to concurrently analyse the concentration of a control gene transcript in parallel assays on aliquots of the same sample, e.g. on aliquots of isolated patient RNA, more preferably to analyse the concentration of the control gene transcript in a one-tube assay reaction to provide the same analytical reaction conditions to both the MN1 transcript and the control gene transcript. The concentration of MN1-encoding transcripts is preferably analyzed by RT-PCR using primers specific for transcripts of MN1, optionally by RT-PCR in one tube concurrent with RT-PCR using primers specific for transcripts of the reference gene. As a reference gene transcript, it is preferred to use the transcript of a housekeeping gene, more preferably the transcript of a housekeeping gene having one copy per haploid genome. Most preferably, the reference gene transcript is selected from the group comprising the transcripts of ABL, β-2-microglobuline and β-glucuronidase genes.

The control gene transcript can be an external RNA that is added to the RNA of the patient sample for further parallel processing or, preferably, the control gene is an endogenous gene transcript. A preferred control gene is ABL (Abelson), located at 9q34. Preferably, the control gene is analysed according to the EAC (Europe against cancer) protocols for reverse transcription (EAC RT) and subsequent PCR on the cDNA (RQ-PCR), which were developed as described in Gabert et al., Leukemia 17, 2318-2357 (2003). Exemplary primers for specific amplification of cDNA derived from ABL transcripts are 5' CCT TCA GCG GCC AGT AGC 3' (Seq ID No. 5) and 5' GGA CAC AGG CCC ATG GTA C 3' (Seq ID No. 6) (published by Beillard et al., Leukemia 17, 2474-2486 (2003)).

The identification of PCR products obtained in RT-PCR of RNA encoding MN1 can be performed by known methods, e.g. by direct detection of amplification products during PCR, preferably during nested PCR, or by gel electrophoresis, preferably followed by hybridization using a nucleic acid probe specific for a nucleic acid sequence partially encoding MN1, preferably using a probe that excludes sequences of the primers used during PCR.

Accordingly, the critical level of MN1 expression can according to one embodiment be determined as a normalized copy number in relation to the copy number of a reference nucleic acid coding sequence, e.g. the ABL encoding nucleic acid sequence.

The critical level of MN1 transcripts is preferably defined in relation to the concentration of transcripts of a reference RNA or single-stranded DNA obtained in a one-tube RT-PCR or PCR, respectively, with the patient RNA sample. The RNA or single-stranded DNA used as a reference can be synthetic or a cDNA, preferably an ABL encoding nucleic acid sequence. The critical level is preferably defined as the normalized copy number of MN1 transcripts, i.e. the quotient of the copy number of MN1 transcripts to the copy number of transcripts of a reference gene, e.g. ABL.

For determination of the levels of transcripts of MN1 and a reference gene, various relevant measurement results obtainable from specific PCR can be used, allowing a quantitative analysis of nucleic acids. Although the mean cycling threshold method is subsequently described as a preferred method for quanitative analysis of transcripts of MN1 and a reference gene, other methods known to the skilled person can be used, including assays using the immobilization of one of amplified DNA and a specific probe, followed by specific determination of amplified DNA hybridized to the probe.

In one embodiment, the determination of the critical level of MN1 as a first step comprises the identification of the mean threshold cycle (also termed cycling threshold) for MN1 transcript and for a reference gene transcript, e.g. derived from the ABL gene. This mean cycling threshold is defined as the mean minimum number of thermal cycles necessary for reaching a pre-selected detection signal by amplification in the respective specific PCR mixture. Effectively, the mean threshold cycle is an arbitrarily chosen signal obtained from the progress of the specific amplification reaction, e.g. by luminescence measurement of a double-strand DNA specific dye, e.g. TaqMan or SYBR Green. The mean threshold cycle can be determined using the Real-Time PCR system available from Applied Biosystems, Foster City, USA.

In the embodiments of the invention, both MN1 and reference gene transcript concentrations can be determined as the threshold cycle necessary to obtain the same degree of amplification, respectively. The determination of the critical level of MN1 as a first step by identification of the threshold cycle is the determination of a crossing point at which the signal obtained from the specific PCR crosses at set signal intensity point that is preferably chosen between the baseline signal and chosen a signal height that is sufficiently low to be within the exponential region of the amplification reaction, e.g. within the exponential section of the signal of the PCR.

In all embodiments, the critical level of MN1 can be calculated from the levels of transcripts of MN1 and reference gene as the quotient of the value determined for MN1 and of the value determined for the reference gene. This quotient implies a normalization of the MN1 level to the reference level.

According to the invention, the critical level of MN1 transcripts of a patient sample is the normalized copy number of MN1 transcripts, e.g. defined as the quotient (mean value of MN1 copy number)/(mean value of reference gene copy number). In the case of the ABL gene transcript as the reference gene transcript, this normalized value is 0.06 to 0.07, preferably 0.066. More precisely, a quotient of MN1 transcripts to ABL gene transcripts in the range of 0.0655 to 0.0665 defines the critical value.

Alternatively, the normalization can additionally include an arithmetical reference to values obtained for MN1 and for the reference gene by analysis of a cell line, e.g. ME1, or by analysis of nucleic acids encoding MN1 and the reference gene having known concentrations, e.g. DNA and/or cDNA. The cell line or nucleic acid, preferably analysed in parallel assays, serve as standards. The arithmetical reference of MN1 and of the reference gene, each separately, to the values obtained for a cell line yields a relative copy number for the MN1 level, whereas the arithmetical reference to known concentrations yields an absolute copy number for the MN1 level. Calculation of the arithmetical reference essentially has no impact onto the determination of normalized level of MN1 according to the invention. In short, the arithmetical reference serves as a control for the performance of the PCR reaction. However, in accordance with the invention, the arithmetical reference refers to both MN1 and the reference gene transcripts and, accordingly, do not impact the critical level of MN1 in relation to the reference gene transcript.

For calculations, the algorithm for the Second Derivative Maximum can be used. This algorithm is available as the LightCycler Relative Quantification Software, Roche Diagnostics, Mannheim, Germany, for the LightCycler Real-Time PCR instrument. In this embodiment, also the absolute copy number of transcripts of MN1 and the reference gene, e.g. ABL, can be determined by comparison to standards of the specific RNA, respectively, having known concentrations of nucleic acids, i.e. in relation to standards having known copy numbers. The nucleic acids can be DNA, e.g. plasmids, or single stranded DNA, e.g. cDNA.

As an example of determination the critical level of MN1 by arithmetical reference, the quotient of the concentration of MN1 transcripts to the concentration of ABL transcripts in a patient sample is determined in relation to the transcript levels of MN1 and the reference gene in a cell line serving as a calibrator. The copy numbers or MN1 and reference gene transcripts can be determined using serial dilutions of cDNA obtained from reverse transcription of total RNA, preferably of total mRNA, e.g. of the patient sample and/or of the reference gene, e.g. the RNA of the ME1 cell line (available from DSMZ, Braunschweig, Germany, under accession number ACC 537).

The critical value in respect of an alternative reference gene transcript can be identified by the skilled person by determination of the factor by which the level of transcripts from ABL differs from the level of transcripts from another reference gene and dividing the quotient identified in respect of ABL by that factor.

SHORT DESCRIPTION OF THE FIGURES

Figure 2:
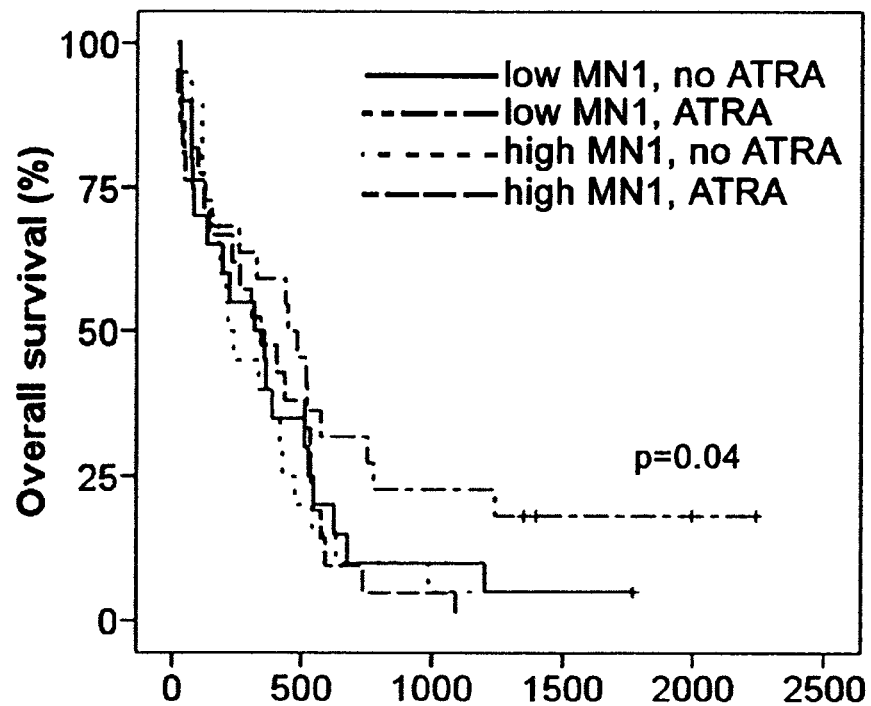
Figure 3:
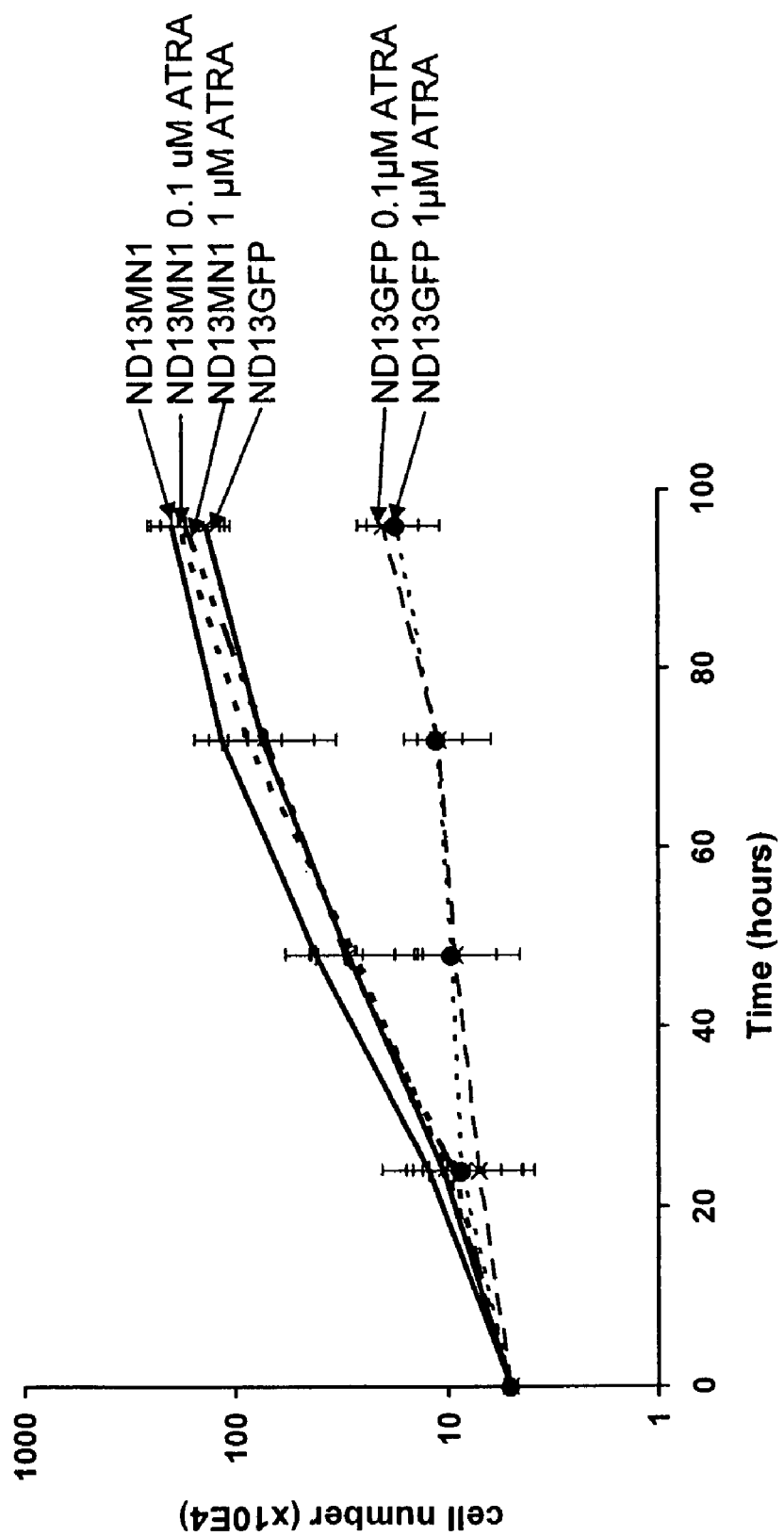
Figure 4:
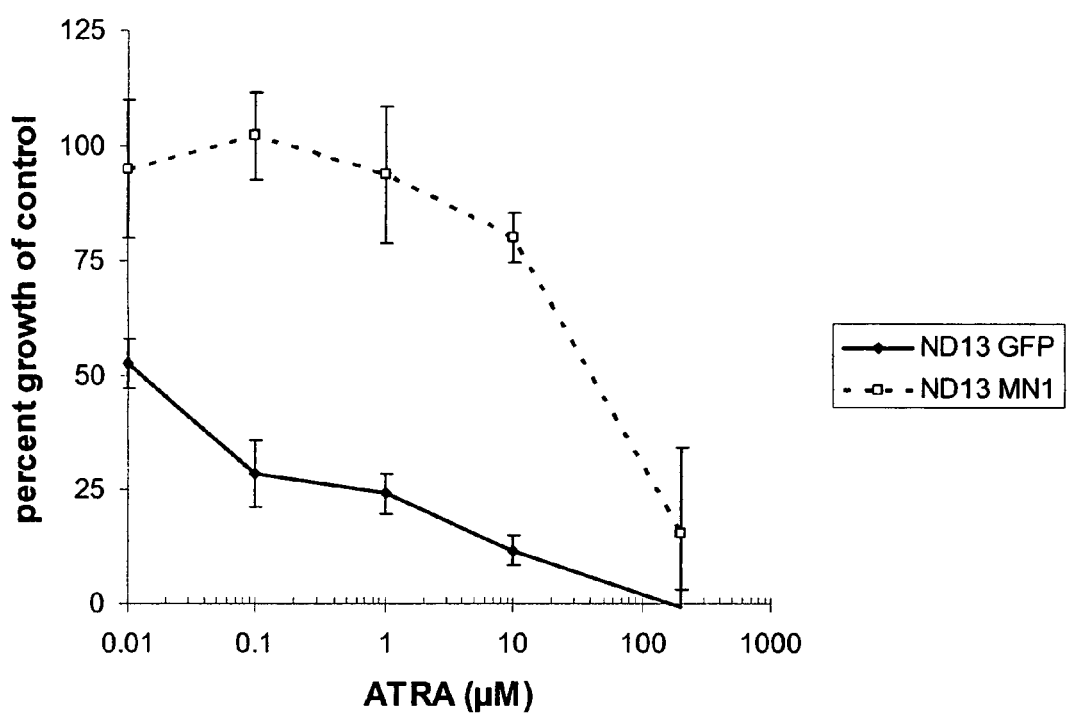

FIG. 1 shows a graph graphical representation of the event-free survival of acute myeloid leukemia patients in respect of the level of MN1 below (low MN1) and above (high MN1) the critical level, each in combination with or without treatment with all-trans retinoic acid (ATRA), FIG. 2 shows the overall survival of patients in respect of the level of MN1 below (low MN1) and above (high MN1) the critical level, each in combination with or without treatment with all-trans retinoic acid (ATRA), FIG. 3 shows in vitro results of the effect of MN1 expression on proliferation and on sensitivity against ATRA, and FIG. 4 shows in vitro results for the determination of the $IC_{50}$ depending on expression of MN1.

DETAILED DESCRIPTION OF THE INVENTION

The present invention is now described in greater detail by way of examples with reference to the figures.

Example 1

Diagnostic Assay for the Determination of the Level of MN1

According to a preferred embodiment of the invention, the level of MN1 is determined as the concentration of transcripts encoding MN1 using RT-PCR. For the isolation of total RNA, preferably of mRNA only, blood cells or bone marrow cells of patients diagnosed with acute myeloid leukemia were extracted as is known in the art.

For RNA extraction, mononuclear cells are isolated from blood or bone marrow cells by Ficoll separation. These cells may be stored frozen, but preferably used fresh for RNA extraction. Total RNA is extracted using TRIZOL reagent (Invitrogen) and, optionally, subsequently purified by a Qiagen RNeasy column (Qiagen). The RNA concentration is determined using standard methods.

As generally known for quantitative PCR, suitable annealing temperatures, cDNA concentrations, buffers can be found by initial test reactions. The threshold number of amplification cycles were preferably determined for each patient sample for the optimal ratio of temperature cycles for amplification of MN1 cDNA and reference cDNA (ABL), respectively, before analysis.

Total RNA (0.1 to 1 µg), preferably mRNA only, is reversely transcribed into cDNA using priming with random hexamer primers. This cDNA, e.g. in an amount of 1/20 to 1/200 of the cDNA obtained from reverse transcription of approximately 1 µg RNA, is subjected to a specific PCR using real-time detection, e.g. the LightCycler (obtainable from Roche Diagnostics, Mannheim, Germany) or Taqman (obtainable from Qiagen, Hilden, Germany) systems or Real-Time PCR system (obtainable from Applied Biosystems, Foster City, USA) according to the manufacturer's instructions. Temperature cycles for PCR amplification of MN1 and ABL in a one tube assay were 95° C. for 15 min, then 45 cycles of 94° C. for 15 s, 53° C. for 25 and 72° C. for 15 s.

For MN1, the following forward-primer was used: GAC-GACGACAAGACGTTGG (Seq ID No. 1), and the reverse-primer: GACAGACAGGCACTGCAAG (Seq ID No 2). As an endogenous control, the Abelson transcript (ABL) was amplified using forward-primer: TGGAGATAA-CACTCTAAGCATAACTAAAGGT (Seq ID No. 3) and reverse-primer: GATGTAGTTGCTTGGGACCCA (Seq ID No. 4).

According to a preferred embodiment of the invention, the physiologic level of MN1 was determined in relation to the copy number of a reference gene transcript, e.g. ABL, serving as the internal reference in the patient sample RNA. The copy numbers of MN1 and reference gene transcript ABL were determined as the relative amount of amplified PCR products in separate RT-PCR procedures (separate assays) or in the same RT-PCR procedure (one-tube assay). For quantitative PCR of cDNA, the cycling threshold was determined as the number of amplification, i.e. temperature cycles necessary to produce a fluorescence signal of a pre-selected intensity or value.

A typical measurement result obtained for an AML patient sample was 190.57 copies MN1 transcript to 3047.47 copies ABL transcript, e.g. giving the critical MN1 level of 0.062531 for MN1/ABL. For absolute quantifications, serial dilutions of DNA of known copy number were used, and the copy number of the patient sample could be determined as the cycling threshold, divided by the relevant dilution factor.

Example 2

Treatment of Acute Myeloid Leukemia Patients with All-Trans Retinoic Acid

The efficacy of the treatment of acute myeloid leukemia patients with all-trans retinoic acid in dependence from the level of MN1 below a critical level is demonstrated for a group of patients from which the M3 subtype was excluded. For exclusion of the M3 subtype of acute myeloid leukemia, standard karyotype analysis from patient peripheral blood or from bone marrow aspirates was performed on all patients as is known in the art. Karyotypes that were excluded were translocations t(15;17)(q22;q21), t(11;17)(q23;q21), t(5;17)(q35;q21), t(11;17)(q13;q21), or t(17;17)(q21;q21).

Patients were above the age of 60. Initially, all 83 patients received treatment according to the AML HD98-B protocol. The induction therapy consisted of ICE (idarubicin 12 mg/m² i.v. days 1 and 3, cytarabine 100 mg/m² cont. i.v. days 1-5, etoposide 100 mg i.v. days 1 and 3) or the same chemotherapy plus ATRA (A-ICE) started after administration of idarubicin and etoposide on day 3 at a dosage of 45 mg/m² from day 3 to 5 and 15 mg/m² from day 6 to 28. Patients achieving CR or partial remission (PR) received a second induction cycle ICE or A-ICE at the same dosage. Patients with refractory disease (RD) after first induction therapy were assigned to a second induction therapy with A-HAE (cytarabine 0.5 g/m²/12 h i.v. days 1-3, etoposide 250 mg/m² i.v. days 4 and 5, ATRA 45 mg/m² days 3-5 and 15 mg/m² days 6-28). Bone marrow evaluation as well as start of the second cycle was scheduled between days 28 and 35. All patients in CR following two cycles of induction therapy were assigned to a first consolidation therapy with HAM (cytarabine 0.5 g/m²/12 h i.v. days 1-3, mitoxantrone 10 mg/m² i.v. days 2 and 3) or A-HAM (along initial randomization) including ATRA at a dosage of 15 mg/m² from day 3 to 28. Allogeneic transplantation was allowed for patients with an HLA-identical family donor on the decision of the local investigator. For conditioning, a combination of fludarabine, cyclophosphamide, idarubicin and etoposide (FCIE) was recommended. Second randomization was performed after completion of first consolidation therapy for patients in CR. Patients were randomized to either a second intensive consolidation therapy IEiv (idarubicin 12 mg/m² i.v. days 1 and 3, etoposide 100 mg/m² i.v. days. 1-5) or to a 1-year oral maintenance therapy IEpo (idarubicin 5 mg p.o. days 1, 4, 7, 10, 13, etoposide 100 mg p.o. days 1 and 13; repeated on day 29 for 12 courses). Patient characteristics were equally distributed between these groups except for a higher proportion of secondary acute myeloid leukemias in the ATRA-treated group.

In FIG. 1, the event-free survival of patients is shown, i.e. survival without relapse after the induction therapy, without failure of induction therapy, without death; the overall survival is shown in FIG. 2 for the same group of patients.

The critical level of MN1 was determined as the relative concentration quotient of patient sample MN1/ABL to MN1/ABL for ME1 cells, i.e. (MN1 transcripts divided by ABL transcripts in patient sample) divided by (MN1 transcripts divided by ABL transcripts in ME1 sample) to 0.0676. This result demonstrates that both absolute and relative quantification measurements essentially yield the same result for the critical level of MN1 in relation to the reference gene, e.g. ABL.

In a second independent group of 142 patients, the relative quotient was determined to 0.0646 under identical conditions.

Accordingly, the critical level of MN1 transcription is found to be 0.06 to 0.07, preferably 0.066 for the relative quotient MN1 transcripts/ABL transcripts for patient samples with arithmetical reference to MN1 and ABL transcript levels determined for the ME1 cell line. The same value was determined for the patient sample quotient of MN1/ABL transcripts.

Event-free survival was equally poor for patients with high expression of MN1 whether receiving ATRA treatment or not. For patients with low levels of MN1 and without ATRA treatment, event-free survival was comparable to that of patients with high MN1 levels. Only patients having an MN1 level below the critical level and receiving ATRA treatment enjoyed significantly improved event-free survival compared to all other patients (p=0.008) and improved overall survival (p=0.04).

From both the event-free survival and the overall survival, a significant increase in the survival of acute myeloid leukemia patients without presence of the M3 subtype could be demonstrated in the treatment with all-trans retinoic acid for patients exhibiting a level of MN1 below the critical level. In contrast, patients exhibiting a level of MN1 above the critical level did not show the drastic improvement in survival rates, the survival rates being effectively independent of the treatment with all-trans retinoic acid.

Example 3

Expression of MN1 Confers Resistance to all-Trans Retinoic Acid in Cell Culture

For a demonstration of the effect of MN1 to confer the resistance against all-trans retinoic acid onto cells and to strongly induce cell proliferation, the mouse cell line ND13 was transduced with a control vector encoding GFP and with an expression vector encoding MN1.

The expression vector encoding GFP contained to the GFP gene under control of the spleen focus-forming virus promoter, integrated into the vector pSF91 (described in detail in Hildinger et al., J. Virol. 73, 4083-4089 (1999)). The MN1 expression vector contained the human MN1 gene under the control of the same promoter in the same vector backbone.

Proliferation results of cell cultures of transduced ND13 cells without ATRA (ctl) and with 0.1 µM all-trans retinoic acid (ATRA) and 1 µM ATRA, respectively, are shown in FIG. 3 for both GFP and MN1 expressing cells.

The results depicted in FIG. 3 clearly show that expression of MN1 resulted in the transformation of ND13 cells, leading to a drastic increase in cell proliferation. In addition, no significant reduction of proliferation was caused by the presence of 0.1 µM ATRA or 1 µM ATRA (top 3 lines at 96 h), resulting in higher cell numbers for both the comparative ND13 cells expressing GFP without ATRA and for ND13 MN1 cells, in the case of ND13 MN1 cells essentially irrespective of the presence of ATRA (no significance). In contrast, presence of 0.1 µM or 1 µM ATRA in the culture of ND13 transduced with the GFP expression vector (bottom two lines) show a significant reduction of proliferation in comparison to transformed cells containing the MN1 expression vector and in comparison to cells containing the GFP expression vector without ATRA (p=0.026 at 24 hours, p<0.001 at 48, 72 and 96 h).

Further, the drastically decreased cytotoxic effect of all-trans retinoic acid for cell lines expressing MN1, i.e. the increase resistance against ATRA conferred by MN1 in comparison to cells expressing a control protein (GFP) was tested by in vitro cultivation of ND13 cells for 72 hours in the dark in the presence of a range of concentrations of all-trans retinoic acid from 0.01 to 200 µM. The growth inhibition is graphically shown in FIG. 4. The $IC_{50}$ for control cells transduced with the GFP expression vector (ND13 GFP) was determined to 0.013 µM ATRA, whereas the $IC_{50}$ for ND13 cells expressing MN1 (ND13 MN1) was determined to 42 µM ATRA, which is a difference by a factor of 3230 (p=0.007).

The drastically reduced cytotoxic effect of ATRA by expression of MN1 in cell culture again shows that MN1 expression dramatically increases resistance of transformed cells against the cytotoxic effect of all-trans retinoic acid.

The invention claimed is:

1. A diagnostic assay for the determination of an indicator for a positive prognosis of a treatment with all-trans retinoic acid (ATRA) of an acute myeloid leukemia patient, excluding the M3 subtype of acute myeloid leukemia patients, the diagnostic assay comprising the determination of the physiologic concentration on meningioma 1 (MN1) in a sample obtained from the acute myeloid leukemia patient to a value below a critical level, indicating a positive prognosis for treatment with ATRA, which value is formed as the quotient of (MN1 transcripts)/(reference gene transcripts), wherein the critical level is 0.06 to 0.07.

2. A diagnostic assay kit for the determination of the concentration of MN1 expression in the diagnostic assay according to claim 1, wherein a sample to be assayed is obtained from a patient being diagnosed with acute myeloid leukemia excluding the M3 subtype and the critical level of MN1, indicative of improved healing when subjected to a therapy implying the administration of all-trans retinoic acid, is determined for the concentration of MN1 transcripts to transcripts from an Abelson (ABL) gene.

3. The diagnostic assay according to claim 1, wherein the internal reference RNA is the transcript of a house-keeping gene.

4. The diagnostic assay according to claim 3, wherein the house-keeping gene transcript is selected from the group comprising the transcripts of the Ableson (ABL) gene, β-2-microglobuline and β-glucoronidase genes.

5. The diagnostic assay according to claim 1, wherein the internal reference ribonucleic acid (RNA) is the transcripts of the Abelson (ABL) gene.

6. The diagnostic assay according to claim 1, wherein the concentration of MN1 ribonucleic acid RNA and of the reference gene transcript is determined by polymerase chain reaction (PCR), and the critical level is determined as the mean threshold cycle.

7. A diagnostic assay kit for the determination of the concentration of MN1 expression in an assay according to claim 1.

8. The diagnostic assay kit according to claim 7, wherein the sample to be assayed is obtained from a patient being diagnosed with acute myeloid leukemia excluding the M3 subtype, and the critical level is determined for the concentration of MN1 transcripts to transcripts from the Abelson (ABL) gene.

9. The diagnostic assay kit according to claim 7, comprising primers specific for RNA encoding MN1 on total RNA obtained from the patient.

10. A diagnostic assay for the determination of acute myeloid leukemia patients, excluding the M3 subtype of acute myeloid leukemia patients, comprising the determination of the physiologic concentration on meningioma 1 (MN1) in acute myeloid leukemia patients to a value below a critical level, which value is formed as the quotient of (MN1 transcripts)/(reference gene transcripts), comprising primers specific for ribonucleic acid RNA encoding MN1, which primers have nucleic acid sequences according to SEQ ID No. 3 and SEQ ID NO. 4, and further including primers specific for the ABL (Abelson) transcript having nucleic acid sequences according to SEQ ID No. 5 and SEQ ID NO. 6.

* * * * *

UNITED STATES PATENT AND TRADEMARK OFFICE
CERTIFICATE OF CORRECTION

PATENT NO. : 8,206,920 B2
APPLICATION NO. : 11/728505
DATED : June 26, 2012
INVENTOR(S) : Michael Heuser et al.

It is certified that error appears in the above-identified patent and that said Letters Patent is hereby corrected as shown below:

In the Specification:

Col. 4, line 26        Please delete "in vitro" and insert --*in vitro*-- therefor.

Col. 7, line 24        Please delete "in vitro" and insert --*in vitro*-- therefor.

Col. 7, line 26        Please delete "in vitro" and insert --*in vitro*-- therefor.

Col. 8, line 4         After "25", please insert --s--.

Col. 10, line 43       Please delete "in vitro" and insert --*in vitro*-- therefor.

Signed and Sealed this
Nineteenth Day of February, 2013

Teresa Stanek Rea
*Acting Director of the United States Patent and Trademark Office*

SEQUENCE LISTING

<160> NUMBER OF SEQ ID NOS: 6

<210> SEQ ID NO 1
<211> LENGTH: 18
<212> TYPE: DNA
<213> ORGANISM: artificial sequence
<220> FEATURE:
<223> OTHER INFORMATION: amplification primer: SEQ ID NO 5: ABL forward

```
                                primer

<400> SEQUENCE: 1
ccttcagcgg ccagtagc                                                 18

<210> SEQ ID NO 2
<211> LENGTH: 19
<212> TYPE: DNA
<213> ORGANISM: artificial sequence
<220> FEATURE:
<223> OTHER INFORMATION: amplification primer: SEQ ID NO 6: ABL reverse
      primer

<400> SEQUENCE: 2
ggacacaggc ccatggtac                                                19

<210> SEQ ID NO 3
<211> LENGTH: 19
<212> TYPE: DNA
<213> ORGANISM: artificial sequence
<220> FEATURE:
<223> OTHER INFORMATION: amplification primer SEQ ID NO 1: MN1 forward
      primer

<400> SEQUENCE: 3
gacgacgaca agacgttgg                                                19

<210> SEQ ID NO 4
<211> LENGTH: 19
<212> TYPE: DNA
<213> ORGANISM: artificial sequence
<220> FEATURE:
<223> OTHER INFORMATION: amplification primer SEQ ID NO 2: MN1 reverse
      primer

<400> SEQUENCE: 4
gacagacagg cactgcaag                                                19

<210> SEQ ID NO 5
<211> LENGTH: 31
<212> TYPE: DNA
<213> ORGANISM: artificial sequence
<220> FEATURE:
<223> OTHER INFORMATION: amplification primer SEQ ID NO 3: ABL forward
      primer

<400> SEQUENCE: 5
tggagataac actctaagca taactaaagg t                                  31

<210> SEQ ID NO 6
<211> LENGTH: 21
<212> TYPE: DNA
<213> ORGANISM: artificial sequence
<220> FEATURE:
<223> OTHER INFORMATION: amplification primer SEQ ID NO 4: ABL reverse
      primer

<400> SEQUENCE: 6
gatgtagttg cttgggaccc a                                             21
```